United States Patent [19]

Carr

[11] Patent Number: 4,496,782
[45] Date of Patent: Jan. 29, 1985

[54] NITRIC ACID RECOVERY BY THE ADIABATIC NITRATION OF NITROAROMATICS WITH FORTIFIED SPENT ACID

[75] Inventor: Richard V. C. Carr, Allentown, Pa.

[73] Assignee: Air Products and Chemicals, Inc., Allentown, Pa.

[21] Appl. No.: 512,289

[22] Filed: Jul. 8, 1983

[51] Int. Cl.³ .............................................. C07C 79/10
[52] U.S. Cl. .................................. 568/934; 568/932; 568/939; 568/940
[58] Field of Search ................ 568/932, 934, 939, 940

[56] References Cited

U.S. PATENT DOCUMENTS

| | | | |
|---|---|---|---|
| 2,012,985 | 9/1935 | Castner | 260/142 |
| 2,256,999 | 9/1941 | Castner | 260/645 |
| 2,402,180 | 6/1946 | Panazoni | 260/645 |
| 2,849,497 | 8/1958 | Buchanan | 260/645 |
| 3,975,452 | 8/1976 | Mayer et al. | 260/645 |
| 4,021,498 | 5/1977 | Alexanderson et al. | 260/645 |
| 4,257,986 | 3/1981 | Milligan et al. | 568/934 |

FOREIGN PATENT DOCUMENTS

| | | | |
|---|---|---|---|
| 703259 | 2/1965 | Canada | 568/934 |
| 715611 | 8/1965 | Canada | 568/934 |
| 1081091 | 8/1967 | United Kingdom | 568/934 |

OTHER PUBLICATIONS

Urbanski, Chemistry and Technology of Explosives, vol. I, The MacMillan Co., New York, 1964, pp. 347 to 349.

Primary Examiner—Leland A. Sebastian
Attorney, Agent, or Firm—Michael Leach; E. Eugene Innis; James C. Simmons

[57] ABSTRACT

A method is provided for denitrifying the aqueous spent acid of mononitration. The nitric acid in the aqueous spent acid is recovered by adiabatically reacting greater than a stoichiometric amount of a mononitroaromatic hydrocarbon with the aqueous spent acid which has been fortified to a nitric acid concentration of at least about 2 wt %. The denitrification method is useful in treating the aqueous spent acid phase from the mononitration stage of a dinitrotoluene process.

25 Claims, 3 Drawing Figures

NITRIC ACID RECOVERY BY THE ADIABATIC NITRATION OF NITROAROMATICS WITH FORTIFIED SPENT ACID

TECHNICAL FIELD

The invention relates to a method for recovering nitric acid. More specifically, the present invention relates to a method for recovering the nitric acid content of a spent acid stream from the mononitration of aromatics.

BACKGROUND OF THE INVENTION

Commercial aromatic nitration processes are generally operated with a mixed acid system comprising sulfuric and nitric acids. A substantial amount of nitric acid is typically lost in an economically and environmentally unsound manner in the spent acid of nitration. For example, conventional dinitrotoluene processes comprise reacting toluene in a first nitration stage to form mononitrotoluene and separating the organic product from the aqueous spent acid phase. The nitric acid in the spent acid phase is usually removed or recovered so that the remaining sulfuric acid can be reconcentrated and recycled. The crude mononitrotoluenes are then nitrated with fresh nitrating acid in a second nitration stage. The dinitrotoluene product is then separated from the aqueous spent acid phase which is recycled to a nitration stage.

Ideally, the nitric acid in the aqueous spent acid of the mononitration stage should be recovered with a minimum of processing and with no risk of discoloration (charring) of the spent acid. One such method involves the extraction of the spent acid with the aromatic hydrocarbon being nitrated in the process. This method removes the excess nitric acid from the spent acid in the form of the mononitro derivative of the aromatic hydrocarbon. Specifically, in a dinitrotoluene process toluene is used to extract the spent acid to recover the nitric acid as mononitrotoluene in a post-reactor. Impractically tight control over the stoichiometric reaction of the aromatic hydrocarbon is necessary to prevent formation of sulfuric acid soluble color bodies which render the final denitrified sulfuric acid black or dark red. "Charred" or black spent acid is unacceptable in the industry particularly if the denitrified spent acid is sent to a phosphate producer.

In another method, treatment of the spent acid of nitration with a variety of oxidizing or reducing agents which destroy the nitrous acid present in spent acid prior to extraction with the aromatic hydrocarbon will prevent the formation of discolored sulfuric acid. The cost of these reagents precludes their use in the industry.

U.S. Pat. No. 2,402,180 discloses a method for the manufacture of trinitrotoluene involving nitration in three steps: mono, di and trinitration stages. The spent acid from the trinitration stage is fortified in the nitrator itself to provide a mixed acid for the dinitration of added mononitrotoluene.

U.S. Pat. No. 2,849,497 discloses a continuous process for the preparation of nitrobenzene which involves contacting the spent acid that remains after the nitration with fresh benzene to use up the major portion of any unreacted nitric acid in the spent acid mixture. The improvement resides in the step of extracting dissolved nitric acid in the crude nitrobenzene product by contacting the crude nitrobenzene with the denitrated waste acid and thereafter denitrating the waste acid containing this nitric acid with fresh benzene.

U.S. Pat. No. 2,012,985 discloses the nitration of aromatic hydrocarbons such as benzene, toluene, xylene and the like using a spent acid resulting from the nitration of an alphatic alcohol containing at least two hydroxy groups, such as nitroglycerine spent acid.

U.S. Pat. No. 2,256,999 discloses a nitration process which is carried out with the utilization of the entire heat of mixing and of reaction, and the absorption of the heat in the contents of the nitrator. The acids and organic compounds are mixed in the nitrator and no attempt is made to cool the reaction. Accordingly, the temperature of the residual or spent acid remaining at the completion of the reaction is raised considerably. This hot residual acid is then concentrated by any desired method to substantially the strength of the initial sulfuric acid without the loss of the heat of reaction. This reconcentrated residual acid is then used in a subsequent nitration cycle.

U.S. Pat. No. 3,975,452 discloses a process for treating the final acid obtained in forming a nitrate of a polyhydric alcohol, the final acid comprising a mixture of sulfuric acid, nitric acid, water and the nitrate. The process comprises mixing the final acid with an aromatic nitro compound, allowing the mixture to stratify whereby the nitrate is dissolved into the aromatic nitro compound as one layer leaving a substantially nitrate-free waste acid layer comprising sulfuric acid, nitric acid and water, and separating the layers. The waste acid obtained in the extraction, which is free from the nitration product, is utilized for the nitration of aromatic compounds or aromatic nitro compounds, especially for the preparation of that aromatic nitro compound which serves as extracting agent in the process.

U.S. Pat. No. 4,021,498 discloses an adiabatic process for the mononitration of nitratable aromatic hydrocarbons which yield a mononitration product containing less than 500 ppm of dinitrated product. In order to insure complete denitration of the mixed acid in the adibatic reaction, the aromatic nitratable compound is used in slight excess over the nitric acid.

U.S. Pat. No. 4,257,986 discloses an improvement in a process for the manufacture of a nitroaromatic compound produced by the mixed acid nitration method. The improvement resides in the refining of the aqueous acid mixture which comprises (a) contacting the spent mixed acid with an oxidizing or a reducing agent under conditions effective for removing contaminent nitrous acid, (b) contacting the aqueous spent acid mixture in step (a) with feed aromatic compound to remove contaminent organics and residual nitric acid and then, if necessary, (c) contacting the remaining acid mixture with sufficient oxidizing agent under oxidizing conditions to remove residual organic components.

SUMMARY OF THE INVENTION

The invention provides a method for the recovery of nitric acid in the spent acid phase from a mixed acid mononitration reaction. The method comprises
 (a) adding a sufficient amount of nitric acid to provide a nitric acid concentration of at least about 2 wt % in the spent acid phase, and
 (b) adiabatically reacting greater than a stoichiometric amount of a mononitroaromatic hydrocarbon with the nitric acid in the spent acid to afford a dinitroaromatic hydrocarbon product and a nitric acid concentration of less than about 0.25 wt %, preferably less than 0.15 wt %, in the spent acid phase.

In a preferred embodiment the invention is incorporated into a process for dinitrating toluene which nitration process comprises (a) nitrating toluene in a first nitration stage with an aqueous mixture of sulfuric and nitric acids to form a mononitrotoluene containing organic phase and a first aqueous spent acid phase containing minor amounts of nitric acid, (b) separating the organic phase from the first aqueous spent acid phase, (c) nitrating the mononitrotoluenes contained in the organic phase in a second nitration stage using a mixture of sulfuric and nitric acids to form dinitrotoluenes in the organic phase and a second aqueous spent acid phase, (d) separating the organic phase from the second aqueous spent acid phase, and (e) recovering dinitrotoluenes from the organic phase.

The method of the invention as applied to the above two stage dinitrotoluene process comprises (f) adding a sufficient amount of nitric acid to afford at least about 2 wt % nitric acid concentration in the first spent acid phase, and (g) adiabatically reacting greater than a stoichiometric amount of mononitrotoluene with the nitric acid in the fortified first spent acid phase to provide dinitrotoluenes and a nitric acid concentration of less than about 0.25 wt % in the first spent acid phase.

The nitric acid may be added to the spent acid phase or a sufficient excess of nitric acid may be added to the mononitration reaction itself to afford a spent acid phase containing at least about 2 wt % nitric acid for the subsequent adiabatic reaction.

As an advantage of the invention the retention of the heat of reaction is used to attain the appropriate temperature to effect near complete removal of the nitric acid from the spent acid phase. Since the amount of nitric acid present in the spent acid phase is the limiting reagent that determines the adiabatic temperature rise of the reaction, it can be metered in accordance with the desired reaction temperature, and thus afford a control over the temperature rise.

As another advantage, the nitric acid is recovered as the dinitro derivative of the mononitroaromatic hydrocarbon which can be separated from the acid phase and recycled to the nitration process for recovery with the dinitro product.

As yet another advantage, unlike the use of an aromatic hydrocarbon for recovering nitric acid in the spent acid, the mononitro derivative does not react with nitrous acid in the spent sulfuric acid phase to form discolored acid. In other words, the process of the invention does not suffer the prospect of discolored acid during the normal operating ranges of excess nitric acid as does the extraction procedure utilizing unsubstituted aromatic hydrocarbons. In fact, this process will tolerate the severe cases of nitric acid concentration ranges of between 0 and about 3.5 wt % in the spent acid phase from the mononitrator.

Still another advantage of this adiabatic process is the avoidance of the cooling water costs associated with the commonly practiced isothermal processes.

A particular advantage of the invention as applied to a dinitrotoluene process is the recovery of nitric acid by adiabatic reaction with mononitrotoluene will not alter the amount of minor dinitrotoluene isomers as these isomers are predetermined during the mononitration step.

DETAILED DESCRIPTION OF THE INVENTION

Figure 1:
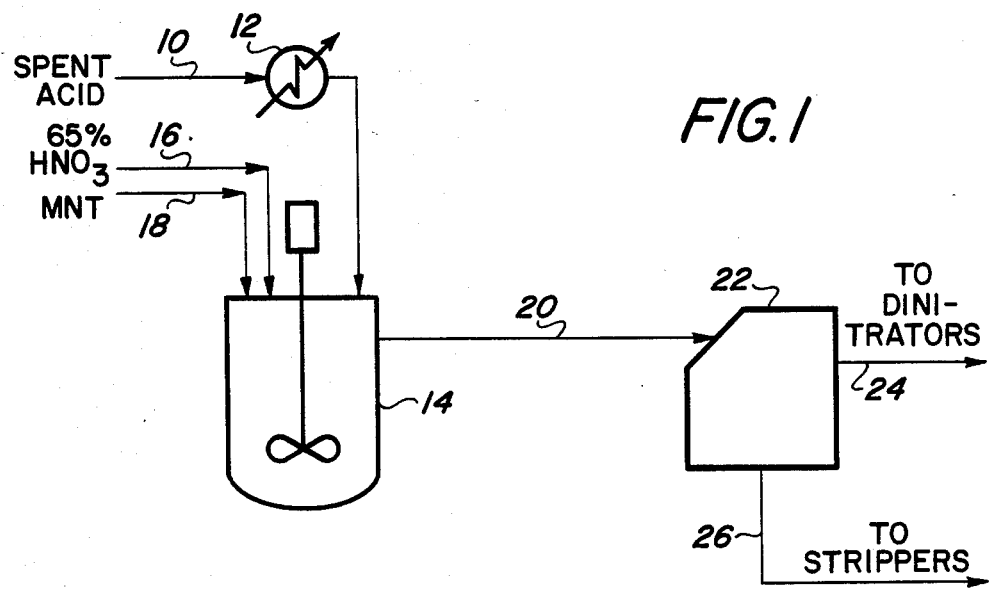
FIG. 1 is a schematic diagram of an embodiment of the invention.

It has been discovered that nitric acid in spent acid from a mononitration process may be recovered by allowing at least a stoichiometric amount and, ideally, at least a stoichiometric excess of a mononitroaromatic hydrocarbon to intimately contact and adiabatically react with the spent acid of nitration. The spent acid of nitration which can be used in the practice of the invention is any spent mixed acid phase from the mononitration of an aromatic hydrocarbon. In other words, the spent acid phase may come from a mononitration stage in the production of mononitroaromatic hydrocarbons or in the two step nitration of aromatic hydrocarbons to dinitroaromatic hydrocarbons. The only requirement for the spent acid is that it contain sulfuric acid in a concentration of at least about 70 wt %. Most industrial mononitration stages are operated so that the spent acid phase also contains nitric acid at about 1 wt % or less, preferably less than about 0.4 wt %.

The nitric acid which is added to the spent acid to raise, or fortify, the nitric acid concentration to at least about 2 wt % can be obtained from any source and be any concentration. It is preferred to use 65% nitric acid which is a common grade used in industry. The nitric acid is added at such a rate to the spent acid to bring the concentration up to about 2 wt % and attain a reaction temperature of at least about 110° C. so the mononitroaromatic hydrocarbon will react at a reasonable rate while not permitting the temperature of the adiabatic reaction mixture to rise too high for safety reasons and to prevent evaporative losses. In other words, the spent acid is fortified to a nitric acid content ranging from at least about 2 wt % to about 3.5 wt %. Preferably the nitric acid concentration should be brought within the range of 2.2 to 3.3 wt %.

Where pressure reaction vessels are not used, the temperature of the adiabatic reaction should be maintained at less than about 115° C., preferably in the range of 110° to 114° C., because it appears to be near optimum with respect to the nitric acid evaporative losses at atmospheric pressure and higher temperatures versus the slow dinitration rate at lower temperatures when the sulfuric acid concentration in the spent acid ranges from about 72-74 wt % as is common in the industry. The use of pressure vessels would of course permit higher temperatures, i.e. greater than about 115° C., and higher rates without evaporation concerns. The absolute upper limit of temperature may be determined by product quality (oxidation) and safety concerns.

Continuous stirred tank reactors of conventional design are routinely operated at 105° to 110° C. for the manufacture of trinitrotoluene. Specially designed continuous stirred tank reactors can be operated at about 140° C. in the adiabatic nitrobenzene process.

Again it should be pointed out that because the temperature of the adiabatic reaction of the mononitroaromatic hydrocarbon with spent acid is controlled by the limiting reagent, nitric acid, the feed metering of the nitric acid should be adjusted in response to the reaction temperature in order to preclude uncontrolled temperature rise.

Suitable mononitroaromatic hydrocarbons for reaction with the fortified spent acid include mononitrobenzene and substituted mononitrobenzenes such as mononitrotoluene, the isomers of mononitro-t-butyl benzene, the isomers of mononitroxylene and the like. It is preferred to use the mononitro derivative of the aromatic hydrocarbon which is nitrated in the process that provides the spent acid to be denitrified. In other words, if the spent acid for denitrification is generated in a process for dinitrating toluene, the spent acid after fortification with nitric acid is ideally contacted with a stoichiometric excess of mononitrotoluene.

In FIG. 1 nitration spent acid from storage in line 10 is heated in heat exchanger 12 by hot water to about 90° C. and introduced into reaction vessel 14. Aqueous nitric acid (65%) in line 16 and mononitrotoluenes in line 18 are also introduced to the reaction vessel with agitation. The addition of the nitric acid is controlled at such a rate as to maintain a temperature of about 110° C. in the reactor. Reactor product containing dinitrotoluene, unreacted excess mononitrotoluene and a reduced level of nitric acid is removed in line 20 and passed into separator 22 where the reactor product is separated into an upper organic phase containing the nitrotoluenes and a denitrified aqueous acid lower phase. The upper organic phase is passed by line 24 for recovery of the nitrotoluenes or, preferably, is passed to dinitrators, not shown, to convert the unreacted mononitrotoluene to the dinitro product for recovery. The aqueous acid phase is passed by line 26 to strippers, not shown, for removal of the remaining amount of nitric acid prior to reconcentration of the aqueous sulfuric acid for recycle.

Figure 2:
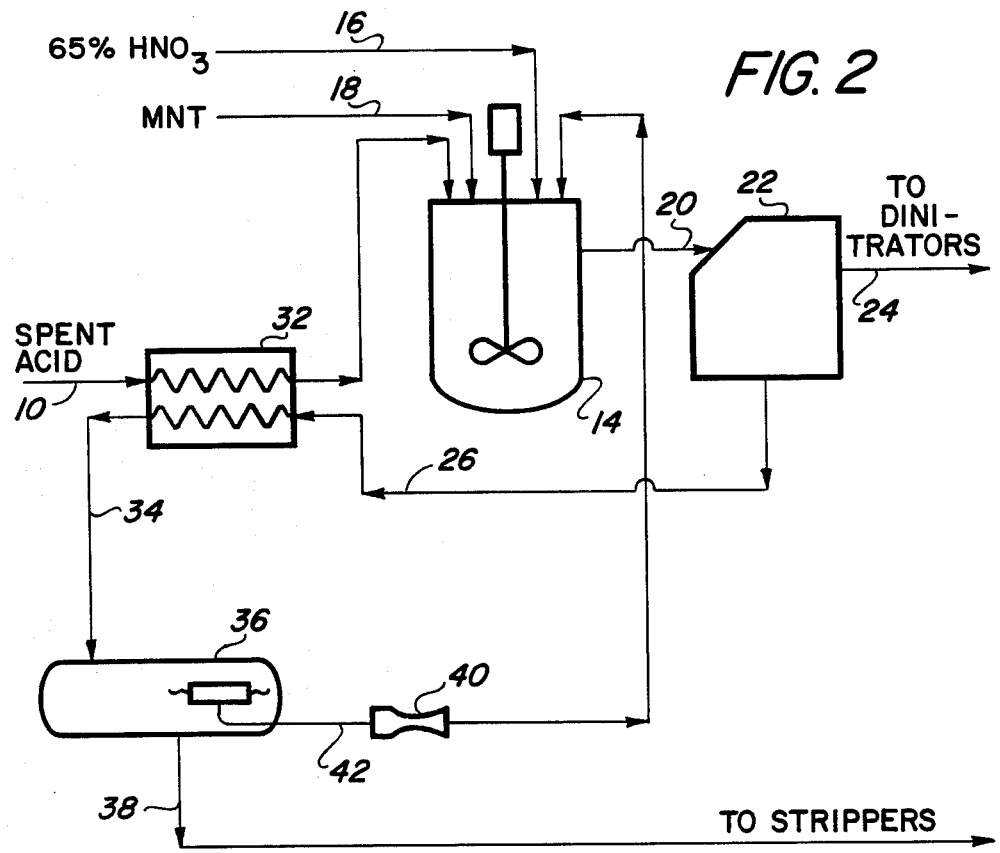
FIG. 2 is a schematic diagram of a preferred embodiment of the invention using denitrified spent acid to heat the fortified spent acid.

FIG. 2 shows a preferred embodiment for reacting mononitrotoluene with nitric acid fortified spent acid. The spent acid in line 10 from storage is heated to about 90° C. in heat exchanger 32 against denitrified aqueous spent acid from separator 22 in line 26. The cooled denitrified aqueous spent acid from the heat exchanger 32 passes by line 34 into surge tank 36. Aqueous spent acid is removed from surge tank 36 in line 38 for further denitrification in strippers, not shown, to provide a spent acid suitable for reconcentration. Separated organics in line 42 from surge tank 36 passes through pump 40 prior to being recycled to reactor vessel 14.

The heat of nitration in reactor 14 will adiabatically raise the temperature of the reaction to about 110° C. and the nitric acid concentration in the reactor overflow 20 will be about 0.15 to 0.25 wt %. However, the amount of mononitrotoluenes dissolved in the 110° C. spent acid from reactor 14 is sufficient (0.3 to 0.4 wt %) to reduce the remaining nitric acid to the 0.1 to 0.15 wt % level by homogeneous nitration in separator 22 having a sufficient minute residence time, for example at least about 8 minutes, preferably 10 minutes. Running the 110° C. spent acid stream 26 directly to strippers will reduce the cost of preheating the acid feed but the organic load may increase steam usage in the stripper to achieve product acid specifications. Therefore, the preferred embodiment shown in FIG. 2 allows for the physical separation of the increased organic load prior to stripping.

Table 1 shows the mass balances of the designated streams for both embodiments shown in FIG. 1 and FIG. 2.

TABLE 1

| Stream No. | 10 | | 16 | | 18 | | 20 | | 24 | | 26 | |
| Stream Name | Spent Acid Feed | | Nitric Acid | | MNT Feed | | Reactor Product | | Rework | | Stripper Feed | |
| Components | LB/HR | % W | LB/HR | % W | LB/HR | % W | LB/HR | % W | LB/HR | % W | LB/HR | % W |
|---|---|---|---|---|---|---|---|---|---|---|---|---|
| Toluene | | | | | 18 | 2.00 | | | | | | |
| MNT | 21 | 0.24 | | | 710 | 80.3 | 405 | 4.15 | 378 | 36.6 | 16 | 0.17 |
| DNT | 14 | 0.16 | | | 130 | 14.7 | 613 | 6.14 | 574 | 55.5 | 69 | 0.77 |
| $HNO_3$ | 36 | 0.40 | 165 | 65.0 | 9 | 1.00 | 19 | 0.19 | 5 | 4.64 | 9 | 0.10 |
| $H_2SO_4$ | 6436 | 72.4 | | | 11 | 1.24 | 6447 | 64.54 | 22 | 2.13 | 6425 | 71.3 |
| $H_2O$ | 2344 | 26.4 | 89 | 35.0 | 4 | 0.50 | 2470 | 24.72 | 5 | 0.58 | 2462 | 27.3 |
| $HNO_2$ | 34 | 0.40 | | | 3 | 0.30 | 36 | 0.36 | | | 36 | 0.39 |
| TOTAL | 8885 | | 254 | | 885 | | 9990 | | 1034 | | 9017 | |

Figure 3:
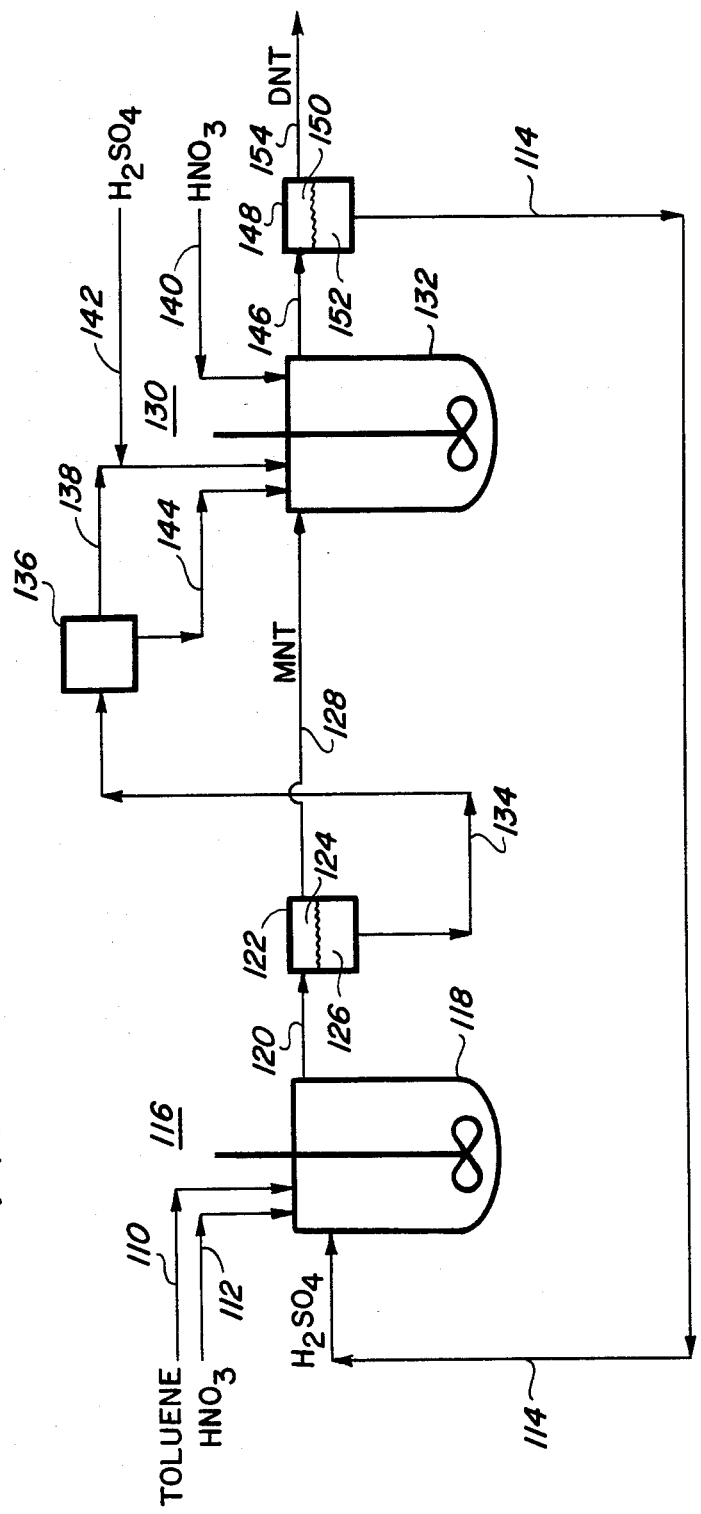
FIG. 3 is a schematic diagram of a dinitration process incorporating the denitrification process of the invention.

Referring now to FIG. 3 which depicts a dinitration process incorporating the present invention, toluene at about 140 l/min in line 110; 60 to 90% aqueous nitric acid at about 90 l/min in line 112; and 80 to 90% aqueous sulfuric acid as cycle acid at about 300 l/min in line 114 are concurrently fed to the mononitration stage 116 which is depicted as comprising a single reaction vessel 118. It is preferred, however, that the mononitration zone 116 comprise about four such reaction vessels connected in series with the overflow rate passing from one reaction vessel to the next being approximately equal to the total flow rate of toluene, nitric acid and sulfuric acid fed into the first reaction vessel. The mononitration reaction medium which is maintained in the mononitration reaction stage 116 at a temperature from about 40° to 70° C. exits via line 120, passes to separator 122 in which the organic phase 124 and the spent aqueous acid phase 126 which compose the mononitration reaction medium are gravity separated.

The organic phase 124 which contains about 0.5 wt % unreacted toluene, 20 wt % dinitrotoluenes and 80 wt % mononitrotoluenes passes through line 128 at about 190 l/min into dinitration stage 130 which may comprise a single reaction vessel 132, but preferably comprises four such reaction vessels connected in series.

The spent acid 126 from separator 122 in line 134 which is about 65 to 80 wt % sulfuric acid and about 0.1 to 1 wt % nitrous and nitric acids at about 40°-50° C., is passed at about 350 l/min to denitrifier/reconcentrator stage 136 which comprises a denitrification process depicted in FIG. 1 or FIG. 2 and a stripper operation where the spent acid stream from the denitrifier is heated to drive off water. A reconcentrated (90–98 wt %) sulfuric acid stream from the denitrifier/reconcentrator stage 136 passes through line 138 at about 235 l/min into dinitration stage 130 along with 60–90% aqueous nitric acid from line 140 at about 100 l/min. Virgin sulfuric acid (90–98%) may be added by line 142, if necessary, or instead of the reconcentrated acid from denitrifier/reconcentrator 136. The organic phase which comprises mononitrotoluenes and dinitrotoluenes from the denitrifier/reconcentrator 136 is passed by line 144 into the dinitration vessel 132.

The dinitration reaction medium, which is at a temperature from about 60° to 90° C. and comprises dinitrotoluenes and spent nitrating acid, passes from reaction vessel 132 via line 146 at about 820 l/min into separator 148 where the dinitrotoluene containing organic phase 150 and the spent aqueous acid phase 152 are separated. The organic phase 150 which contains about 99.8 wt % dinitrotoluene product passes in line 154 to a washing and product recovery stage, not shown. The spent aqueous acid phase 152 is conveyed at about 300 l/min by line 114 as "cycle acid" to the mononitration stage 116.

The denitrification/reconcentration stage 136 would use plant mononitrotoluene as the denitrifying agent. Since the amount of toluene in plant mononitrotoluene may be expected to vary from 0.5 to 8 wt % and the nitric acid in the spent acid may vary from 0.2 to 0.6 wt %, the nitric acid recovery from the spent acid must be able to tolerate these extremes without the risk of spent acid charring which is due in large part to the normal process operating streams for unreacted toluene and nitric acid leaving the mononitrators.

In the above-described process, up to 15–20 wt % of unreacted toluene in the plant mononitrotoluene will not lead to acid charring since excess nitric acid is added to achieve the required 20° C. adiabatic temperature rise. Because the heats of nitration of toluene and mononitrotoluene are proximal, the heat release to the reaction versus nitric acid consumed will be close enough to obviate temperature excursions regardless of the amount of toluene present in the mononitrotoluene. With respect to the variation in the nitric acid concentration in the spent acid phase, the temperature control feeding of fortifying nitric acid to the denitrification reaction will nullify the effect of any deviations in the nitric acid excess up to about 2.2 wt % nitric acid in the spent acid.

As an additional feature of the described denitration process, instead of adding fortifying nitric acid to the spent acid from the mononitration process, the mononitration process can be operated such that the spent acid would already contain the 2.2 wt % nitric acid as it leaves the last mononitrator vessel. The advantages of this approach, higher mononitration rate/better toluene conversion, may be offset by the inability to maintain the type of control on the excess nitric acid necessary to control the adiabatic temperature rise in the denitrification reactor with mononitrotoluene. However, a compromise nitric acid level in the mononitration spent acid of about 1.0 to 1.5 wt % may be distinctly advantageous.

In order to maintain the sulfuric acid concentration of the stripper product, or reconcentrator, acid at the process design level, additional 98% sulfuric acid will have to be added to the process at some point due to the increase in dinitrotoluene production obtained by the denitrification process. However, there is, in effect, no increased sulfuric acid usage in the scheme, because of the additional dinitrotoluene obtained. If the additional sulfuric acid is added to the mononitration feed acid (cycle acid), the following benefits may be had: increased rate of mononitration, increased rate of adiabatic nitration of mononitrotoluenes with fortified spent acid and decreased by-product formation in the mononitrators.

EXAMPLES

In the following runs the spent acid phase was prepared by duplicating the composition of the spent acid from the mononitrator in a dinitration process. The apparatus used to simulate the process of the invention comprised a 50 ml continuous stirred tank reactor in series with a 400 ml continuous stirred tank reactor which, in turn, was connected in series with a separator vessel. Because heat losses were expected to be great the system was well insulated and some heating was, by necessity, applied to the two reactors to maintain the theoretical adiabatic temperature. In addition, in order to ascertain the extent of nitration occurring homogeneously in the separator, the reactor overflow was collected in a flask immersed in a 110° C. oil bath and samples were withdrawn for analysis at the appropriate residence time.

The two reaction vessels were initially charged with 80 wt % sulfuric acid containing a small amount (0.03 wt %) of nitric acid to prevent corrosion. The reactors were brought to within 5° C. of temperature by applying heat. Agitation of the reactor contents was then commenced and the feeds introduced.

Table 2 shows the experimental data with regards to Runs 1–5.

TABLE 2

| Run | Spent Acid Feed (wt %) | Sample | Residence Time (min) | °C. | HNO$_3$ Wt % | Toluene Mole % | MNT Mole % | DNT Mole % | % HNO$_3$ Depletion |
|---|---|---|---|---|---|---|---|---|---|
| 1 | 71.3 H$_2$SO$_4$ | Feed | — | 40$^a$ | 1.97 | 7.46 | 92.5 | 0.00 | 0.00 |
|  | 0.3 HNO$_2$ | Reactor 1 | 0.90 | 84 | — | 3.72 | 95.4 | 0.93 | — |
|  |  | Reactor 2 | 7.21 | 108 | 0.41 | 0.22 | 86.8 | 13.0 | 79.2 |
|  |  | Separator | 10.0 | 110 | 0.33 | 0.00 | 82.8 | 17.2 | 83.3 |
| 2 | 71.3 H$_2$SO$_4$ | Feed | — | 35$^a$ | 2.20 | 8.01 | 92.0 | 0.00 | 0.00 |
|  | 0.3 HNO$_2$ | Reactor 1 | 1.18 | 88 | — | 3.03 | 95.5 | 1.39 | — |
|  |  | Reactor 2 | 9.41 | 110 | 0.15 | 0.00 | 88.4 | 11.6 | 93.2 |
|  |  | Separator | 10 | 110 | 0.11 | 0.00 | 86.9 | 13.1 | 95.0 |
| 3 | 72.1 H$_2$SO$_4$ | Feed | — | 35$^a$ | 2.14 | 13.4 | 86.6 | 0.00 | 0.00 |
|  | 0.3 HNO$_2$ | Reactor 1 | 1.25 | 90 | — | 9.96 | 87.1 | 2.97 | — |
|  |  | Reactor 2 | 10.0 | 114 | 0.08 | 0.92 | 88.8 | 10.3 | 96.3 |
|  |  | Separator | 10.0 | 115 | 0.07 | 0.00 | 89.9 | 11.0 | 96.7 |
| 4 | 72.1 H$_2$SO$_4$ | Feed | — | 35$^a$ | 2.16 | 13.2 | 86.8 | 0.00 | 0.00 |
|  | 0.3 HNO$_2$ | Reactor 1 | 0.95 | 91 | — | 4.91 | 92.7 | 2.41 | — |
|  |  | Reactor 2 | 7.62 | 114 | 0.11 | 0.00 | 83.7 | 16.3 | 94.9 |
|  |  | Separator | 10.0 | 110 | 0.09 | 0.00 | 79.7 | 20.3 | 95.3 |

TABLE 2-continued

| Run | Spent Acid Feed (wt %) | Sample | Residence Time (min) | °C. | HNO$_3$ Wt % | Toluene Mole % | MNT Mole % | DNT Mole % | % HNO$_3$ Depletion |
|---|---|---|---|---|---|---|---|---|---|
| 5 | 71.7 H$_2$SO$_4$ | Feed | — | −35$^a$ | 2.22 | 7.70 | 78.8 | 13.5 | 0.00 |
|   | 0.3 HNO$_2$ | Reactor 1 | 0.83 | 92 | — | 5.08 | 79.9 | 15.0 | — |
|   |   | Reactor 2 | 6.67 | 114 | 0.13 | 0.17 | 68.1 | 31.7 | 94 |
|   |   | Separator | 10.0 | 110 | 0.11 | 0.00 | 63.6 | 36.4 | 95 |

$^a$Prior to heat exchanger

It can be seen from the data in Table 2 that a spent acid stream which comprises about 72 wt % sulfuric acid and about 0.3 wt % nitrous acid and is fortified to a little over 2 wt % nitric acid can be denitrified by adiabatically reacting a stoichiometric excess of mononitrotoluenes. Run 1 shows a 83.3% nitric acid depletion of the aqueous acid phase in the separator while Runs 2-5 show at least about 95% nitric acid depletion. It is believed that the lower level of nitric acid depletion in Run 1 compared to Runs 2-5 is due to shorter contact time in the reactors and a slightly lower temperature. The toluene which is introduced into the reactors as a component of the plant mononitrotoluenes is almost totally nitrated in the second reactor and is completely nitrated in the separator. This nitration of the toluene explains the increase in mole % of the mononitrotoluenes shown in Reactor 1 in each run. With the exception of Run 3 the mononitrotoluene decreased from Reactor 1 to Reactor 2 to the separator demonstrating that the mononitrotoluenes were consumed to yield dinitrotoluenes.

STATEMENT OF INDUSTRIAL APPLICATION

The process of this invention provides a means for denitrifying the spent acid of nitration from an industrial nitration process without losing a substantial amount of the nitric acid in the spent acid in an economically and environmentally unsound manner.

I claim:

1. A method for the recovery of nitric acid in the spent acid phase from a mixed acid mononitration reaction which comprises
   (a) adding a sufficient amount of nitric acid to provide at least about 2 wt % nitric acid concentration in the spent acid phase from the mononitration reaction, and
   (b) adiabatically reacting a mononitroaromatic hydrocarbon in greater than a stoichiometric amount with the nitric acid in the spent acid phase to afford a dinitroaromatic hydrocarbon product and a nitric acid concentration of less than about 0.25 wt % in the spent acid phase.

2. The method of claim 1 in which the spent acid phase is fortified to a nitric acid concentration of about 2 to 3.5 wt %.

3. The method of claim 2 in which the nitric acid concentration of the fortified spent acid phase is between 2.2 to 3.3 wt %.

4. The method of claim 1 in which the adiabatic reaction of step (b) is performed at about atmospheric pressure.

5. The method of claim 4 in which the temperature of the reaction is maintained at about 115° C. or less.

6. The method of claim 4 in which the temperature of the adiabatic reaction is maintained at about 110° to 114° C.

7. The method of claim 1 in which the adiabatic reaction of step (b) is performed at greater than one atmospheric pressure.

8. The method of claim 7 in which the temperature of the adiabatic reaction is greater than about 115° C.

9. The method of claim 1 in which the nitric acid concentration of the spent acid phase after the adiabatic reaction is less than about 0.15 wt %.

10. The method of claim 1 in which the mononitroaromatic hydrocarbon is mononitrobenzene or mononitrotoluene.

11. In a process for nitrating toluene which comprises:
    (a) nitrating toluene in a first nitration stage with an aqueous mixture of sulfuric acid and nitric acid to form a mononitrotoluene containing organic phase and a first aqueous spent acid phase containing nitric acid,
    (b) separating the organic phase from the first aqueous spent acid phase,
    (c) nitrating the mononitrotoluenes in the organic phase in a second nitration stage using a mixture of sulfuric and nitric acids to form dinitrotoluenes in the organic phase and a second aqueous spent acid phase,
    (d) separating the organic phase from the second aqueous spent acid phase, and
    (e) recovering dinitrotoluenes from the organic phase,
the method for recovering the nitric acid in the first spent acid phase which comprises
    (f) adding a sufficient amount of nitric acid to afford at least about 2 wt % nitric acid concentration in the first spent acid phase, and
    (g) adiabatically reacting mononitrotoluene in greater than a stoichiometric amount with the nitric acid in the first spent acid phase to provide dinitrotoluenes and a nitric acid concentration of less than about 0.25 wt % in the first spent acid phase.

12. The process of claim 11 in which the first spent acid phase is fortified to a 2 to 3.5 wt % nitric acid concentration.

13. The process of claim 12 in which the nitric acid concentration of the fortified spent acid phase is between 2.2 to 3.3 wt %.

14. The process of claim 11 in which the adiabatic reaction of step (g) is performed at about atmospheric pressure.

15. The process of claim 14 in which the adiabatic reaction is maintained at a temperature of about 115° C. or less.

16. The process of claim 14 in which the adiabatic reaction temperature is maintained at about 110° to 114° C.

17. The process of claim 11 in which the adiabatic reaction of step (g) is performed at greater than one atmosphere pressure.

18. The process of claim 17 in which the adiabatic reaction is maintained at a temperature greater than about 115° C.

19. The process of claim 11 in which the nitric acid concentration of the first spent acid phase after the adiabatic reaction is less than about 0.15 wt %.

20. The process of claim 11 in which at least a stoichiometric excess of mononitrotoluene is used for the adiabatic reaction of step (g).

21. The process of claim 11 in which the adiabatic reaction of the mononitrotoluene with the nitric acid in the first spent acid phase is commenced in a nitrator vessel and finished in a separator.

22. The process of claim 11 in which the mononitration step (a) is performed so as to provide a first spent acid phase containing at least about 2 wt % nitric acid.

23. The process of claim 22 in which the fortifying nitric acid is added to the mononitration step.

24. The process of claim 11 in which the fortifying nitric acid is added to the first spent acid phase.

25. The method of claim 1 in which the amount of mononitroaromatic hydrocarbon is greater than a stoichiometric excess.

* * * * *